United States Patent
Bennett

Patent Number: 5,766,143
Date of Patent: *Jun. 16, 1998

[54] COTTON SWABS WITH EXPANDED TIPS

[75] Inventor: Robert Bennett, Easton, Conn.

[73] Assignee: Chesebrough-Ponds' USA Co., Division of Conopco, Inc., Greenwich, Conn.

[*] Notice: The term of this patent shall not extend beyond the expiration date of Pat. No. 5,531,671.

[21] Appl. No.: 863,752

[22] Filed: May 27, 1997

Related U.S. Application Data

[62] Division of Ser. No. 414,984, Mar. 31, 1995, Pat. No. 5,709,010, which is a division of Ser. No. 412,048, Mar. 28, 1995, Pat. No. 5,531,671.

[51] Int. Cl.⁶ ............................................. A61M 35/00
[52] U.S. Cl. ................. 604/1; 15/118; 15/209.1; 15/244.1
[58] Field of Search .................. 604/1–3; 600/572, 600/569; 15/208, 209.1, 210.1, 244.1

[56] References Cited

U.S. PATENT DOCUMENTS

| | | |
|---|---|---|
| Re. 22,478 | 5/1944 | Perkins . |
| 661,151 | 11/1900 | McCausland . |
| 1,669,966 | 5/1928 | Beardsley . |
| 1,731,715 | 10/1929 | Dunlap . |
| 1,903,664 | 4/1933 | Yutts . |
| 2,153,144 | 4/1939 | Gilfillan . |
| 2,218,525 | 10/1940 | Decker . |
| 2,255,887 | 9/1941 | Katz . |
| 2,308,537 | 1/1943 | Perkins . |
| 2,362,704 | 11/1944 | McGivern . |
| 2,365,838 | 12/1944 | Perkins . |
| 2,430,648 | 11/1947 | Schonrock . |
| 2,813,286 | 11/1957 | Strader . |
| 2,914,409 | 11/1959 | Mayson . |
| 3,020,660 | 2/1962 | Scherotto . |
| 3,090,080 | 5/1963 | Pellicone et al. . |
| 3,255,494 | 6/1966 | Bloch et al. . |
| 3,333,515 | 8/1967 | McGlynn . |
| 3,402,646 | 9/1968 | Hall . |
| 3,452,650 | 7/1969 | Cobb . |
| 3,586,380 | 6/1971 | Albeckoff . |
| 3,661,666 | 5/1972 | Foster et al. . |
| 4,259,955 | 4/1981 | Ritter . |
| 4,457,756 | 7/1984 | Kern et al. . |
| 4,718,889 | 1/1988 | Blasius, Jr. et al. . |
| 4,767,398 | 8/1988 | Blasius, Jr. . |
| 4,820,259 | 4/1989 | Stevens ............... 604/1 |
| 4,887,994 | 12/1989 | Bedford . |
| 5,000,202 | 3/1991 | Stepan ............... 604/1 |
| 5,085,633 | 2/1992 | Hanifl et al. . |
| 5,127,899 | 7/1992 | Schmerse, Jr. . |
| 5,147,288 | 9/1992 | Schiavo . |
| 5,158,532 | 10/1992 | Peng et al. . |
| 5,212,847 | 5/1993 | Melcher et al. . |
| 5,364,792 | 11/1994 | Stone . |
| 5,531,671 | 7/1996 | Bennett ............... 604/1 |

FOREIGN PATENT DOCUMENTS 990564  6/1976  Canada .

*Primary Examiner*—John G. Weiss
*Assistant Examiner*—Dennis Ruhl
*Attorney, Agent, or Firm*—Milton L. Honig

[57] ABSTRACT

A cotton swab is described whose stick is formed from an elongate stem with a conical member at each end flared outwardly and having a hollow center. The hollow flared conical members provide expanded swab ends rendering the tips softer and larger yet employing less cotton and paper in its manufacture. A die-cut paper used for forming the swab stick and a manufacturing process are also described.

3 Claims, 1 Drawing Sheet

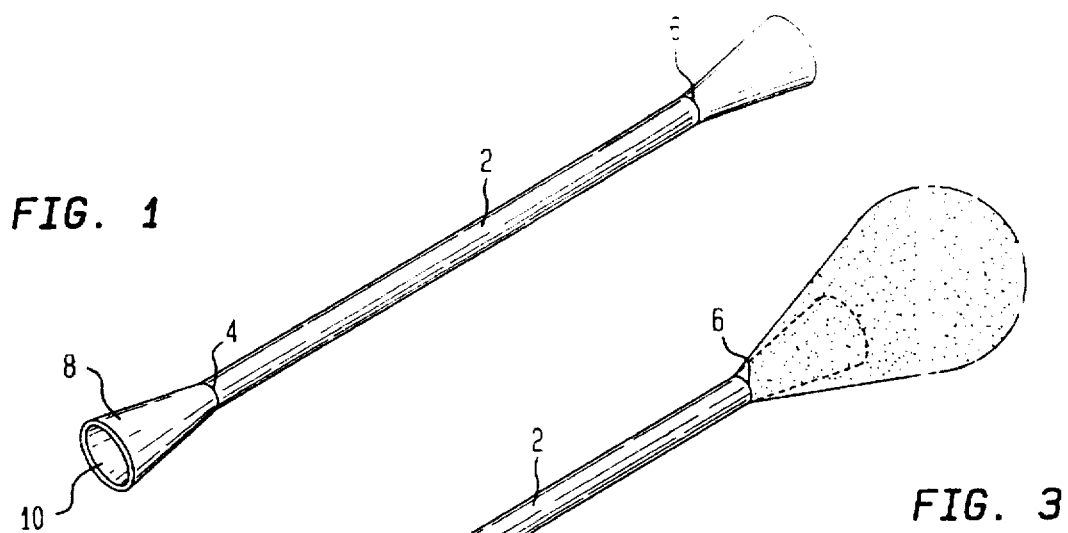
FIG. 1
FIG. 2
FIG. 3
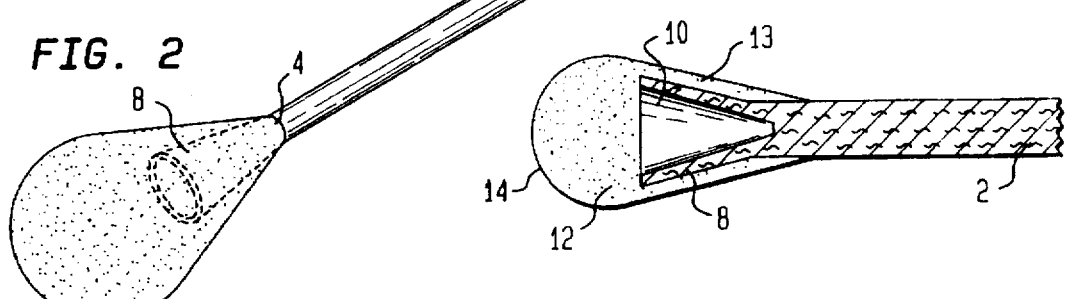
FIG. 4
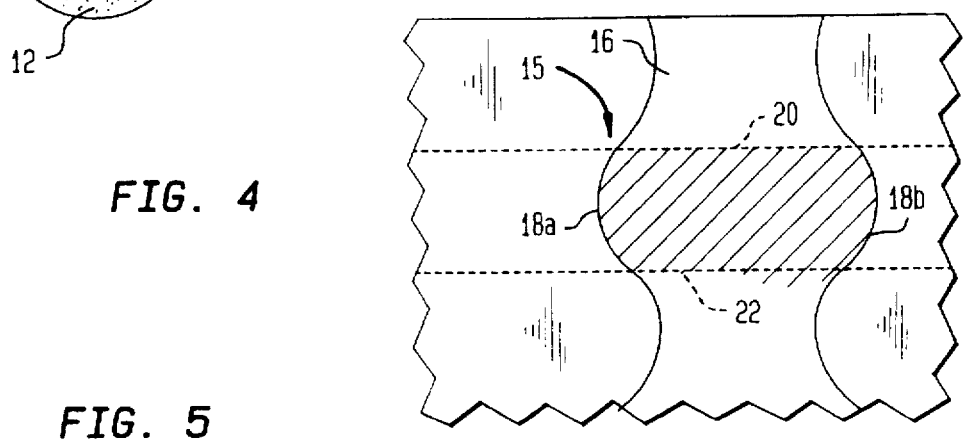
FIG. 5
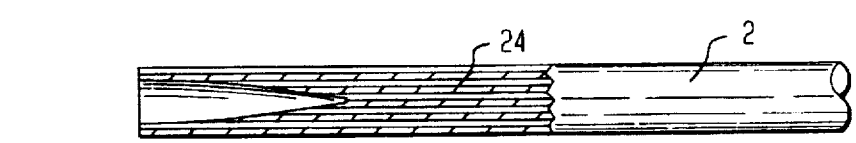
FIG. 6
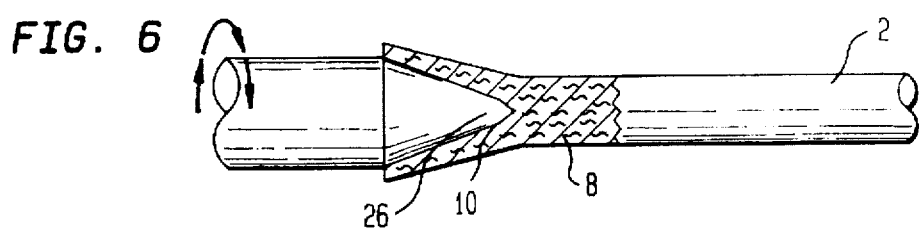

COTTON SWABS WITH EXPANDED TIPS

This Application is a Divisional of Ser. No. 08/414,984 filed Mar. 31, 1995, now U.S. Pat. No. 5,709,010, which in turn is a Divisional of Ser. No. 08/412,048 filed Mar. 28, 1995 which issued as U.S. Pat. No. 5,531,671 on Jul. 2, 1996.

BACKGROUND OF THE INVENTION

1. Field of the Invention

The invention relates to cotton swabs useful in cleaning the ear or applying cosmetics.

2. The Related Art

Swabs having an absorbent covering on the tip and an elongated stem are well known. Cotton is generally used as the absorbent tip covering material. Stem materials are often of wood, rolled paper or plastic. Conventional swabs are typically constructed by applying the absorbent covering directly to the distal ends of the stem. An adhesive may be used to more firmly hold the absorbent covering in place upon the swab.

Cost and performance problems have long been associated with traditional swabs. U.S. Pat. No. 5,127,899 (Schmerse, Jr.) raises the issue of eardrum damage when swabs are improperly applied to clean the outer ear. The patent suggests that injuries may be avoided by positioning a flat disc at each of the distal ends of the swab beneath the cotton coverings. This disc is sized to prevent entry of the swab into the human ear canal. Although a useful improvement, the flat disc increases the rigidity of the cotton covered end tips rendering the ends harder. There are also manufacturing difficulties with providing a flat disc to the ends of the swab stem.

U.S. Pat. No. 4,718,889 (Blasius, Jr. et al.) discloses the use of a resilient cushion positioned between the end of the stem and the absorbent covering. This resilient cushion is intended to provide some degree of protection against damage in the event that the stem does protrude through the absorbent covering. However, the stem is not rendered substantially softer and is also more difficult to manufacture.

It is evident that further improvements are necessary in swab technology. These improvements should focus on softer ends, bigger cotton tips and less construction materials to reduce costs.

Accordingly, it is an object of the present invention to provide a swab with softer ends than those currently available.

Another object of the present invention is to provide a swab with larger tips yet fashioned from less materials including less cotton and less paper forming the stem.

SUMMARY OF THE INVENTION

A swab is provided that includes:

an elongate stem with first and second ends opposite one another;

a conical member formed at each of the first and second ends, the conical member flaring outwardly and having a hollow center; and an absorbent covering surrounding each of the conical members.

The stem and conical member are formed from a die-cut paper consisting of a flat cellulosic sheet with mirror image curved left and right edges cut along a length of the sheet. Upper and lower edges at opposite ends of the sheet have straight cut edges parallel to one another.

A further aspect of the invention is that of a process for preparing the swab. Steps of the process include:

(a) preparing a swab stick by die-cutting a paper to achieve mirror image curved left and right edges cut along a length thereof;

(b) rolling the die-cut paper into a stick;

(c) contacting ends of the stick with a spinning mandrel to form a conical member flaring outwardly and having a hollow center; and (d) placing an absorbent covering around each of the conical members.

BRIEF DESCRIPTION OF THE DRAWING

The above features, advantages and objectives of the present invention will be more fully appreciated through the following detailed discussion, reference being made to the drawing consisting of:

FIG. 1 which is a plan perspective view of the stem and conical members according to the present invention;

FIG. 2 which is a plan perspective view of the swab according to the present invention;

FIG. 3 which is an enlarged cross-sectional view of the swab end according to the present invention;

FIG. 4 which is a top plan view of the die-cut according to the present invention;

FIG. 5 which is an enlarged cross-sectional view of a swab stick tip, prior to flaring, according to the present invention; and FIG. 6 which is a view similar to FIG. 5 except illustrating the action of a spinning mandrel to flare the tip into a conical member.

DETAILED DESCRIPTION

Now it has been discovered that a cotton swab can be provided with expanded ends to benefit consumers through a wider, softer tip. Manufacturing costs are also reduced because of less cotton and paper necessary in the manufacture of the swab. By using a spinning mandrel to widen the end of the stick, a conical shaped member results. Cotton is applied to that member. A soft hollow tipped cotton swab results.

FIG. 1 illustrates an elongate stem 2 with first and second ends 4, 6 at opposite extremities from one another. A conical member 8 is formed at each of the first and second ends 4, 6. Each of the conical members has a hollow center 10.

FIG. 2 illustrates the complete swab structure. An absorbent covering 12 surrounds each of the conical members 8. Cotton is the most preferred absorbent covering. However, synthetic or other natural materials of flexible and absorbent properties can also be utilized. For example, the absorbent covering could be formed of rayon fibers, polyurethane or other foamed or fibered synthetic polymers.

FIG. 3 best illustrates hollow center 10 and its full outwardly flaring structure. The hollow conical member permits a larger, softer tipped cotton absorptive covering. Much less cotton is necessary along the flared surface 13 to achieve a cotton end having a size equivalent to that of a swab without the hollow center. Yet, safety and performance are not compromised because most of the cotton absorbent covering is concentrated at tip 14.

FIG. 4 illustrates a die-cut paper 15 from which is formed the stem and conical members of the swab. The die-cut paper is fashioned from a flat cellulosic sheet 16 with mirror image curved left and right edges 18a, 18b cut down a length thereof. At opposite ends of the die-cut paper are upper and lower edges 20, 22 straight cut and parallel to one another.

Stem and conical members are unitarily formed as a swab stick in a process beginning with the preparation of the die-cut paper shown in FIG. 4. Upon preparation, the die-cut paper 15 is tightly rolled. Adhesives may optionally be spread on the die-cut paper to assist in maintaining the stick form. FIG. 5 illustrates the resultant swab stick 24. FIG. 6 illustrates the next process step wherein a tip of a spinning mandrel 26 penetrates hollow 10 of the rolled swab stick 24. Conical members 8 are formed by the flaring action of the spinning mandrel. Thereafter, cotton fibers are applied in the conventional well-known manner to each of the swab stick ends thereby forming the cotton absorptive covering.

The foregoing description and drawing illustrate selected embodiments of the present invention and in light thereof various modifications will be suggested to one skilled in the art, all of which are within the spirit and purview of this invention.

What is claimed is:

1. A swab comprising:

an elongate stem with first and second ends opposite one another, the stem being formed from a single die-cut paper rolled into a swab stick shape, each of the ends formed of less paper than central sections of the stem rendering the ends softer than the center; and an absorbent covering surrounding each of the first and second ends.

2. The swab according to claim 1 wherein the absorbent covering is cotton.

3. The swab according to claim 1 wherein the die-cut paper comprises a flat cellulosic sheet having upper and lower edges cut straight and parallel to one another and side edges which form the ends of the stem having non-parallel segments along left and right edges.

* * * * *